US009933376B2

(12) United States Patent
Chang et al.

(10) Patent No.: US 9,933,376 B2
(45) Date of Patent: Apr. 3, 2018

(54) APPARATUS AND METHOD FOR ANALYZING DEFECTS BY USING HEAT DISTRIBUTION MEASUREMENT

(71) Applicant: Korea Basic Science Institute, Daejeon (KR)

(72) Inventors: Ki Soo Chang, Daejeon (KR); Seon Young Ryu, Chungcheongbuk-do (KR); Woo June Choi, Daejeon (KR); Geon Hee Kim, Sejong (KR)

(73) Assignee: Korea Basic Science Institute, Daejeon (KR)

( * ) Notice: Subject to any disclaimer, the term of this patent is extended or adjusted under 35 U.S.C. 154(b) by 222 days.

(21) Appl. No.: 14/647,772

(22) PCT Filed: Nov. 26, 2013

(86) PCT No.: PCT/KR2013/010797
§ 371 (c)(1),
(2) Date: May 27, 2015

(87) PCT Pub. No.: WO2014/084574
PCT Pub. Date: Jun. 5, 2014

(65) Prior Publication Data
US 2015/0316496 A1 Nov. 5, 2015

(30) Foreign Application Priority Data

Nov. 27, 2012 (KR) .................. 10-2012-0135492

(51) Int. Cl.
*G01N 25/72* (2006.01)
*H01L 21/66* (2006.01)

(52) U.S. Cl.
CPC ............. *G01N 25/72* (2013.01); *H01L 22/12* (2013.01)

(58) Field of Classification Search
CPC combination set(s) only.
See application file for complete search history.

(56) References Cited

U.S. PATENT DOCUMENTS 7,173,245 B2 2/2007 Shakouri et al.
7,429,735 B2 9/2008 Lueerssen et al.
(Continued)

FOREIGN PATENT DOCUMENTS

KR 10-2010-0058012 A 6/2010
WO 2009/149103 A1 12/2009

OTHER PUBLICATIONS

Office Action issued in Japanese application No. 2015-543997, dated Apr. 26, 2016 (5 pages).
(Continued)

*Primary Examiner* — Lisa Caputo
*Assistant Examiner* — Nasir U Ahmed
(74) *Attorney, Agent, or Firm* — Osha Liang LLP

(57) ABSTRACT

The present invention provides a method for analyzing defects by using heat distribution measurement, comprising: a sample loading unit for loading a sample to check whether or not there is a defect through heat distribution characteristics; a light source for radiating visible light onto the sample; a power supply unit for generating a driving signal in order to periodically heat the sample; a detection unit for detecting reflected light from the surface of the sample; and a signal generator for synchronizing the detection unit with the driving signal of the power supply unit.

10 Claims, 4 Drawing Sheets

(56) References Cited

U.S. PATENT DOCUMENTS

| | | |
|---|---|---|
| 2004/0032581 A1 | 2/2004 | Nikoonahad et al. |
| 2004/0235205 A1* | 11/2004 | Levy ............... G01N 21/211 |
| | | 438/14 |
| 2005/0002435 A1* | 1/2005 | Hashimoto ........... G01N 25/72 |
| | | 374/43 |
| 2007/0057184 A1* | 3/2007 | Uto ................. G01N 21/95607 |
| | | 250/310 |
| 2009/0084659 A1 | 4/2009 | Underberg et al. |
| 2009/0245322 A1 | 10/2009 | Hudgings et al. |
| 2010/0279213 A1* | 11/2010 | Levy ............... G01B 11/24 |
| | | 430/30 |
| 2012/0035863 A1 | 2/2012 | Kuwabara |

OTHER PUBLICATIONS

International Search Report issued in PCT/KR2013/010797, dated Jan. 7, 2014 (4 pages).
English translation of Written Opinion issued in PCT/KR2013/010797, dated Jan. 7, 2014 (6 pages).

* cited by examiner

APPARATUS AND METHOD FOR ANALYZING DEFECTS BY USING HEAT DISTRIBUTION MEASUREMENT

TECHNICAL FIELD

The present invention relates to an apparatus and method for analyzing defects using heat distribution measurement, and more particularly, to an apparatus and method for analyzing defects capable of measuring hot spots caused by flaws (or defects) of a semiconductor device using a submicron spatial resolution and a non-contact method. The apparatus can analyze positions of the defects with high accuracy by overlapping the hot spots with a semiconductor fine pattern image.

BACKGROUND ART

Recently, due to the high integration and miniaturization of semiconductor devices, and complexity of the manufacturing process thereof, various defects that cause problems in the operations of the devices have been generated. Such defects serve as the cause for reduction of performance and yield of the semiconductor device, and thus the semiconductor device manufacturing companies are putting a lot of efforts into addressing this problem.

In general, the defects are known to be caused by a mask misalignment, contaminants, voids, and non-uniformity of an impurity concentration inside the semiconductor devices, etc. The types of defects include open/short of a metal interconnection, increased local resistance, abnormal contact resistance, micro-plasma leakage of an oxide layer, oxide layer breakdown, and device latch-up, etc.

Recently, due to the fine pattern and high integration of the semiconductor devices, the yield is significantly decreased by small sizes (for example, about 1 μm or less) of internal defects, process defects, or pattern defects. Thus, the importance of the defect analysis has become significant in increasing the productivity. It is because that the production costs can be saved from the increased productivity.

When the defects were generated in the semiconductor device, the method of determining the cause of the defects is as follows. After the manufacturing process is completed, the electrical defects of the device are determined and then the positions of the defects are analyzed with accuracy of within several micro-meters using a variety of non-destructive methods (thermal emission microscopy, photon emission microscopy, scanning acoustic microscopy, etc.). Then, the semiconductor wafer is cut at a point where a defect is assumed to exist using a focused ion beam (FIB), and the cut section is enlarged and observed through a scanning electron microscope (SEM). The causes of the defects can also be analyzed using a composition analysis equipment.

Many types of defects such as a metal short, resistive open, micro-plasma leakage, oxide layer breakdown, and device latch-up in the semiconductor device cause a hot spot.

Therefore, semiconductor manufacturing companies use a semiconductor defect inspection technique such as infrared thermal emission technique. The technique detects infrared thermal emission by the hot spot generated from the semiconductor defects using a mid-infrared (wavelength in a range of 3 μm to 5 μm) microscope. However, in infrared thermal emission technique, the physical limit of spatial resolution is about 3 μm due to the optical diffraction limit, and thus, there is a limit on the accuracy of defect position tracking in the highly integrated and fine patterned semiconductor device.

With the rapid progress of the fine pattering and increase of the degree of integration by the development of the semiconductor manufacturing process techniques, the semiconductor manufacturing companies have required defect analyzing tools of the higher spatial resolution than that of the commercialized defect inspection equipment.

A new method was reported in various ways. It is a thermoreflectance microscopy technique. In this technique, ultraviolet or visible light is illuminated onto the sample through the optical microscope, the distribution of reflectivity change due to the hot spot of the sample is measured by a phase-lock thermal reflection method, and then the heat distribution of the sample is derived from the measured result. Heat distribution measurement/analysis techniques in the semiconductor devices using the new method have been reported.

For example, U.S. Pat. No. 7,173,245 "Submicron thermal imaging method and enhanced resolution (super-resolved) ac-coupled imaging for thermal inspection of integrated circuits" discloses an invention which relates to the thermoreflectance microscope based system and the semiconductor device thermal analysis.

Further, U.S. Pat. No. 7,429,735 "Methods of thermoreflectance thermography" discloses an invention for improving the spatial resolution of the thermal images by using a confocal microscope principle in addition to the thermoreflectance microscope principle.

Further, US Pat. No. US2009/0084659 "High performance CCD-based thermoreflectance imaging using stochastic resonance" discloses an invention for improving the thermal resolution by adding the stochastic resonance (digital signal processing) principle to the thermoreflectance microscope.

However, there are still many problems in which these characteristic measurement methods have been little utilized for the defect analysis of the semiconductor device so far. Some methods may have to cut the sample, and some methods need an excessive amount of time, etc. When the semiconductor device is analyzed, the sample wafer may get damaged in wafer cutting process, which may cause the defect analysis impossible.

Furthermore, since various types of materials such as a metal, a dielectric, a semiconductor material, and the like are exposed on the surface of the semiconductor device, it may be difficult to effectively measure the heat distribution using the common thermoreflectance microscope.

DISCLOSURE

Technical Problem

The present invention is directed to providing a new and previously unprovided defect analysis method for analyzing a defect using a heat generation phenomenon.

The present invention is also directed to providing an apparatus to measure a hot spot distribution generated from a defect of a semiconductor device as a non-contact method with a spatial resolution of 1 μm or less.

The present invention is also directed to providing an apparatus to track and analysis a defect position with high accuracy by overlapping the defect position with a semiconductor fine pattern image.

The present invention is also directed to providing an apparatus to more effectively measure a heat distribution for various types of material exposed on a semiconductor device, etc.

Technical Solution

One aspect of the present invention provides a defect analysis apparatus using heat distribution measurement, the apparatus including: a sample loading unit configured to load a sample to determine whether or not there is a defect through heat distribution characteristics; a light source configured to illuminate the sample; a power supply unit configured to generate a driving signal in order to periodically heat the sample for localized heat at a defect point of the sample; a first detection unit configured to detect light reflected from a surface of the sample; and a signal generator configured to synchronize the first detection unit with the driving signal of the power supply unit.

Preferably, the apparatus may further include a control unit and an image processing unit, and the control unit may measure a change of reflectivity due to a temperature change at the defect point of the sample by using a phase-lock thermal reflection method and convert the measured result to a heat distribution. Further, the control unit and the image processing unit may obtain the heat distribution as a function of a wavelength and derive a wavelength range capable of appropriately observing the heat distribution at the defect point.

The apparatus may further include a first beam splitter, the first beam splitter may deliver a beam radiated from the light source to the sample loading unit and deliver a delivered beam from the sample loading unit to the first detection unit.

Preferably, the first detection unit may be triggered up to multiple times for a cycle of a temperature-modulation.

The apparatus may further include a second beam splitter, the second beam splitter may deliver a delivered beam from the sample loading unit to a second detection unit, and a spectroscope may further be provided on a front end of the second detection unit.

Another aspect of the present invention provides a defect analysis method using heat distribution measurement, the method comprising: lighting visible light onto a sample to determine whether or not there is a defect through heat distribution characteristics; supplying a power source for generating a driving signal in order to periodically heat the sample for localized heat at a defect point of the sample; detecting light reflected from a surface of the sample; and generating a signal for synchronizing a detection unit with the driving signal of a power supply unit.

Preferably, the method may further include measuring a change of reflectivity due to a temperature change at the defect point of the sample by using a phase-lock thermal reflection method; and converting the measured result to a heat distribution.

Preferably, the method may further include measuring a degree of dependence of a wavelength on a thermoreflectance coefficient by using a beam delivered from a sample loading unit and determining an optimal wavelength.

The method may further include delivering a beam radiated from a light source to a sample loading unit and delivering a delivered beam from the sample loading unit to the detection unit.

The method may further include triggering of the detection unit by multiple times for a cycle of a temperature-modulation.

Advantageous Effects

According to embodiments of the present invention described above, the semiconductor manufacturing companies require the spatial resolution higher than that of the defect inspection apparatus which is currently commercialized, and thus, there is an effect that is possible to respond to their requirement.

Further, as a spectral imaging equipment is provided in the thermoreflectance microscope, the wavelength dependency of the thermoreflectance coefficient which is different according to the material and structure of the sample is measured and then the optimal wavelength is selected through the wavelength dependency. It is possible that the thermal image of the sample is achieved by the optimal wavelength with the high resolution and sensitivity. In result, the semiconductor defect position can be tracked and analyzed with high accuracy.

MODES OF THE INVENTION

Hereinafter, exemplary embodiments of the present invention will be described in detail with reference to the accompanying drawings. However, the present invention is not limited to the exemplary embodiments disclosed below, but can be implemented in various forms. The following exemplary embodiments are described in order to enable those of ordinary skill in the art to embody and practice the invention.

Figure 1:
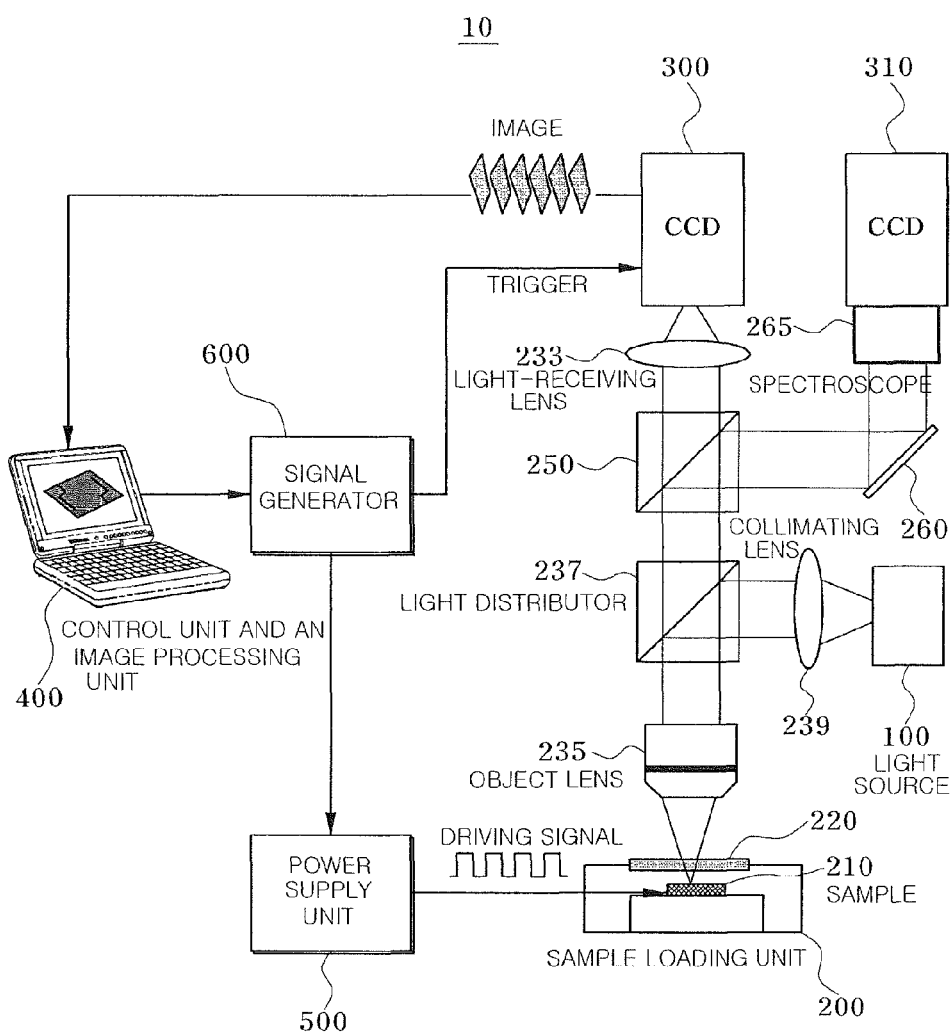
FIG. 1 is a schematic view illustrating a configuration of a defect analysis apparatus according to an embodiment of the present invention.

FIG. 1 is a schematic view illustrating a configuration of a defect analysis apparatus according to an embodiment of the present invention.

Referring to FIG. 1, the defect analysis apparatus according to the embodiment of the present invention includes a light source 100, a sample loading unit 200, a first detection unit 300, a control unit and an image processing unit 400, a power supply unit 500, a signal generator 600, a lock-in correlator (not shown), a first light distributor 237, and various lenses 233, 235, and 239. Meanwhile, a second beam splitter 250, a spectroscope 265, and a second detection unit 310 may be additionally provided in the defect analysis apparatus of the embodiment of the present invention. The added units are units for performing detection for each wavelength by the second detection unit 310 through the spectroscope 265 and selecting an optimal wavelength for each sample when wavelength dependency on the change of reflectivity due to a temperature change of the sample is measured. Although the above units are not essential to the present invention, they may more effectively serve a function in the defect analysis. This will be described below in detail.

The light source 100 provides light in which beams having a plurality of wavelengths in a visible wavelength region are mixed. The light source 100 may use a broadband light source (e.g. a white light source, a light-emitting diode (LED), and a solid-state light source) and a wavelength filter (not shown) for selecting only or the LED having a specific wavelength in a range of 10 nm to 50 nm. A collimating lens 239 for emitting the light source as a parallel beam may be included in an emission region of the light source 100.

The first and second detection units 300 and 310 may include a plurality of light signal detectors including a charged coupled device (CCD), a photo detector, an avalanche photo diode (APD), a photo multiplier tube (PMT).

Meanwhile, the first beam splitter 237 delivers a beam radiated from the light source 100 to the sample loading unit 200 and delivers a beam delivered from the sample loading unit 200 to the first detection unit 300. The second beam splitter 250 distributes the beam delivered from a sample to the first detection unit 300 and the second detection unit 310. Since the second beam splitter 250 is not directly required for measurement of the heat temperature distribution, it may be selectively removed. The control unit and the image processing unit 400 consists of hardware including the power supply unit 500 and the signal generator 600 for synchronizing the first and second detection units 300 and 310 with a driving signal of the power supply unit 500 and software including a processing unit (not shown) which processes the measured signal. Although connection lines of the control unit and the image processing unit 400 of the embodiment of the present invention are schematically illustrated, the control unit and the image processing unit 400 may be implemented to include a function that controls the detection units, a vacuum chamber, a light source, or the like through the connections thereto in an actual implementation.

The control unit and the image processing unit 400 may be synchronized with the second detection unit 310, or not. These will be described in more detail. The wavelength dependency of the thermoreflectance coefficient for each position (a surface material) of the sample is obtained by measuring that of the reflectivity change due to the temperature change. A temperature change may be given to an entire surface of the sample by using a thermoelectric cooler (TEC) to which the sample is attached or to an active region of the sample by biasing the driving signal from the power supply unit. In the former, in order to obtain the wavelength dependency of the reflective change, multiple reflectance images are obtained at each temperature in the spectroscope (e.g., 20° C., 30° C., 40° C., etc.) and an average of the images may be used. In the other case, a phase-lock thermal reflection method may be used. The later only requires the synchronization of the second detection unit 310 with a driving signal of the power supply unit.

According to the embodiment of the present invention, an electrical signal is applied to an object, which can generate heat by the electric signal, and at the same time, visible light is radiated onto the object through an optical microscope or a transparent window, a distribution of the reflected light is detected, for example, by a CCD camera, and thus, the heat distribution of the object is measured by measuring a reflectivity distribution according to the heat distribution of the object.

More specifically, the sample is temperature-modulated at a specific frequency f, and a driving signal from the power supply unit 500 is periodically applied so that heating and cooling of the sample are periodically repeated by the driving signal. For example, a current or a voltage which is periodically changed by the power supply unit 500 may be applied to the sample. A periodic temperature change of the sample is caused by the driving signal which periodically heats and cools as described above. In this case, light reflected from the sample may be detected by the CCD which is the first detection unit 300. The CCD which is the first detection unit 300 is triggered up to multiple times (e.g., twice or more) in a cycle of the temperature-modulation, and thus, multiple (e.g., twice or more) images may be obtained in the cycle of the temperature-modulation of the sample. Data obtained through the CCD is transmitted to the control unit and the image processing unit 400 to be processed.

The signal generator 600 serves to generate the two different periodic signals with specific frequencies for both the temperature-modulation on the sample and the trigger for the CCD of the first detection unit 300, and at the same time, perform synchronization so that the first detection unit 300 is triggered up to multiple times (e.g., twice or more) during a cycle of the temperature-modulation.

According to the above-described method of the embodiment of the present invention, an amount of temperature change is proportional to an amount of change of reflectivity as in the following equation 1. Here, k, which refers to a thermoreflectance coefficient, has a value in a range of approximately $10^{-2}$ to $10^{-5}$. That is, the heat temperature distribution may be measured through the change of the reflectivity.

$$\Delta T = \left(\frac{1}{R}\frac{\partial R}{\partial T}\right)^{-1}\frac{\Delta R}{R} = k^{-1}\frac{\Delta R}{R} \qquad (1)$$

Since a relative amount of the change ($\Delta R/R$) of the reflectivity is proportional to an amount of the change ($\Delta T$) of the temperature ($\Delta R/R = k\Delta T$), the measured result is shown as relative heat distribution information corresponding to the sample.

When heat characteristics of various types of material such as a metal, a dielectric layer, a semiconductor layer, or the like formed on a semiconductor substrate in a semiconductor device manufacturing process are measured and defect analysis is performed, each of the various types of material may have an appropriate heat characteristic in different wavelength band. Therefore, it is preferable to choose the optimal wavelength band according to the material or the region to be measured. In the case in which the semiconductor substrate on which a uniform pattern is formed is continuously monitored, the appropriate wavelength band is preselected and continuously utilized. Further, in the case in which the object of an unknown sample is measured, an investigation for optimal wavelength band of the light source is preceded by the spectroscope 265 and the second detection unit 310. For example, in the case in which the object of the unknown appropriate wavelength band is measured, the heat distribution information of the sample is determined using the spectroscope 265 and the second detection unit 310 for each wavelength band. In this case, the light source is delivered to the spectroscope 265 and the second detection unit 310 using the second beam splitter 250, and then a heat distribution image may be obtained for each wavelength using the spectroscope 265 to find the optimal wavelength band.

After performing a series of operations, when the appropriate wavelength band according to the object (or the specific area of the object) is determined, the object is measured at the corresponding wavelength band using the calculated appropriate wavelength band. Meanwhile, the selection of the appropriate wavelength may utilize a filter or the like on an inside or front end of the light source 100.

Figure 2:
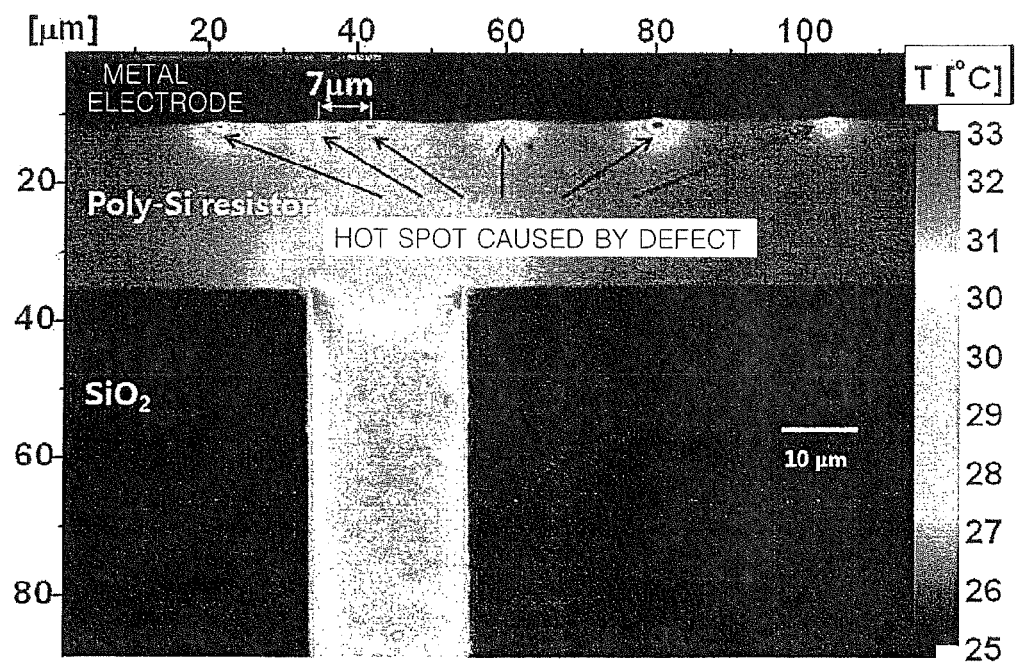
FIG. 2 is an image in which a heat distribution with respect to a defect analysis position is measured according to an embodiment of the present invention.

FIG. 2 is an image in which a heat distribution with respect to a defect analysis position is measured according to an embodiment of the present invention.

The image represents a heat distribution of a microresistance device manufactured for testing the above-described method. It is shown that a hot spot caused by a number of defects that are present at an interface between a metal electrode and a polysilicon (poly-Si) resistor may be detected with a high resolution. Further, it is shown that a spatial resolution of FIG. 2 may be 1 μm or less.

Therefore, according to the embodiment of the present invention, when a metal wiring short or an abnormal contact resistance of the semiconductor device occurs, heat is generated and the heat may be tracked with high accuracy. More specifically, the hot spot distribution generated from the defects of the semiconductor device is measured using the spatial resolution of 1 μm or less and a non-contact method. The positions of the defects are tracked and analyzed with high accuracy by overlapping the hot spot with a semiconductor fine pattern image.

The semiconductor device has a surface of the sample configured of various types of material, most semiconductor devices have a multi-layer structure, and thus, the wavelength dependency of the thermoreflectance coefficient is very large. Further, a passivation layer, which is transparent for a visible light, is formed on the surface of the semiconductor device, and thus, there is a characteristic in which a value of the thermoreflectance coefficient is rapidly changed according to the wavelength of light. For example, the value of the thermoreflectance coefficient is rapidly changed by the change of a thickness of the passivation layer of several nanometers. Therefore, according to the wavelength of light used in the thermoreflectance measurement of the sample, the heat distribution may not be measured when the light having the wavelength in which the value of the thermoreflectance coefficient is close to 0 is used, on the contrary, the heat distribution may be measured with high sensitivity when the light having the wavelength in which the thermoreflectance coefficient is maximum is used.

Therefore, in order to perform highly sensitive and high-resolution semiconductor defect inspection using the thermoreflectance microscope, it is required that the optimal wavelength with the maximum thermoreflectance coefficient is selected for each sample. In this case, the thermoreflectance coefficient k is changed according to the wavelength of light used in measurement of the change of reflectivity due to the temperature change of the sample, the type of sample material, and the thickness of the layer as well as the type of material that constitutes the layer due to the interference effect of the light generated in a multi-layer structure when the sample has the multi-layer structure.

Figure 3:
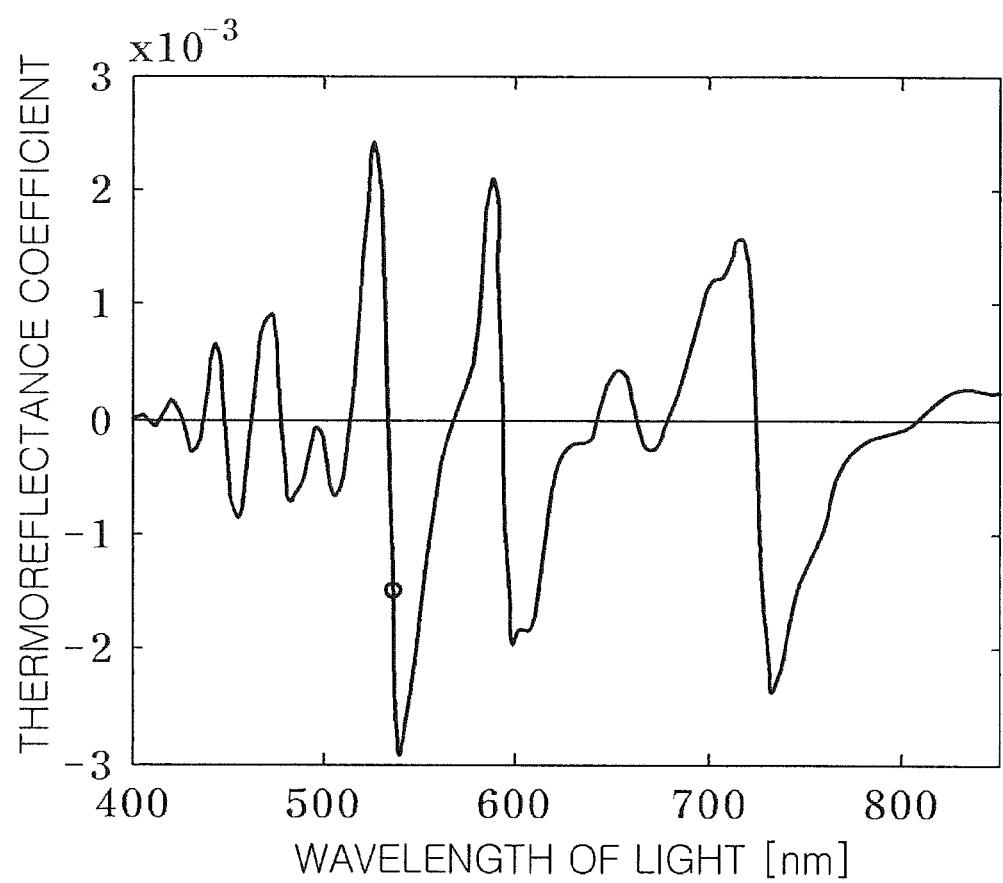
FIG. 3 is a graph illustrating an example in which a thermoreflectance coefficient is changed for each wavelength due to an interference effect of light of a semiconductor device.

FIG. 3 is a graph showing an example in which a thermoreflectance coefficient is changed for each wavelength due to an interference effect of light of a semiconductor device, and shows the thermoreflectance coefficient spectrum for a semiconductor including a $SiN_x$ passivation layer, poly-Si, $SiO_2$, and a Si substrate. Referring to FIG. 3, it may be shown that the thermoreflectance coefficient is rapidly changed according to the wavelength of the light used in thermoreflectance measurement, and there is also the case of the wavelength in which the value of the thermoreflectance coefficient is close to 0.

Meanwhile, in the thermoreflectance microscope system, a second beam splitter, a mirror, a light-receiving lens, a spectral imaging system are provided therein, and the spectrum of the light reflected from the surface of the sample is measured. Further, when the relative spectrum of the change of the reflectivity, $$\frac{1}{R}\frac{\partial R}{\partial T},$$

is measured on the surface of the sample while a temperature of the sample is changed, the wavelength dependency of the thermoreflectance coefficient, $k(\lambda)$ may be measured.

Figure 4:
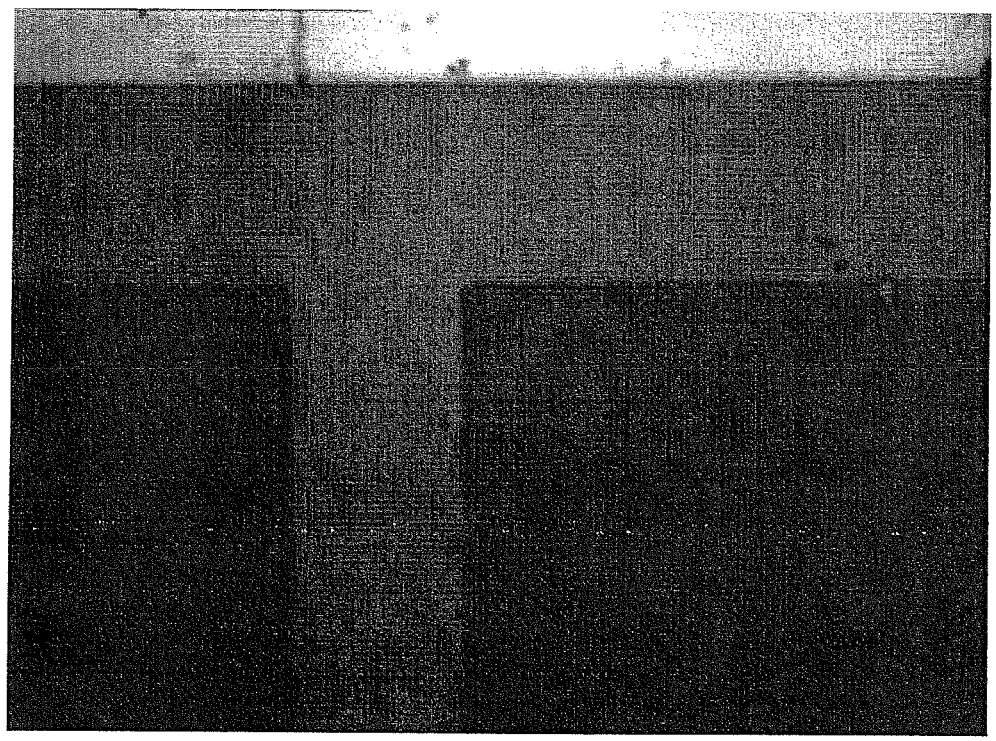
FIG. 4 is an image obtained by a commercialized semiconductor defect inspection apparatus for comparison with a heat distribution image according to the embodiment of the present invention.

FIG. 4 is an image, which is obtained by the conventional technique, obtained by a commercialized semiconductor defect inspection apparatus for comparison. The image of FIG. 4 is provided for comparison with the image of FIG. 2. The commercialized apparatus uses the detection principle of the mid-infrared thermal emission.

As a result of the comparison, it has been experimentally seen that the analysis apparatus according to the embodiment of the present invention measures hot spots generated from the fine defects with high power and high resolution. In the case of the commercialized semiconductor defect inspection apparatus using the existing infrared thermal image, a physical limit of the spatial resolution is about 3 μm. Therefore, there is a limit in the accuracy of the defect position track of the high integrated and fine pattern semiconductor.

While preferable embodiments with respect to an apparatus for analyzing defects using heat distribution measurement according to the present invention have been described, the invention is not limited thereto and may be embodied with various modifications within the scope of the appended claims, detailed description and the accompanying drawings, and such embodiments are also within the scope of the invention.

The invention claimed is:

1. A defect analysis apparatus using heat distribution measurement, the apparatus comprising:
    a sample loading unit configured to load a sample to determine whether or not there is a defect through heat distribution characteristics;
    a light source configured to radiate light onto the sample;
    a power supply unit configured to generate a driving signal in order to periodically heat the sample at a defect point of the sample;
    a first detection unit configured to detect light reflected from a surface of the sample; a signal generator configured to synchronize the first detection unit with the driving signal of the power supply unit; and
    a control unit; and
    an image processing unit,
    wherein the control unit measures a change of reflectivity due to a temperature change based on a defined relation at the defect point of the sample and converts the measured change to a heat distribution to analyze the positions of the defects by detecting hot spots.

2. The apparatus of claim 1, wherein the control unit and the image processing unit obtain the heat distribution according to a wavelength.

3. The apparatus of claim 1, further comprising a first beam splitter, wherein the first beam splitter delivers a beam radiated from the light source to the sample loading unit and delivers a delivered beam from the sample loading unit to the first detection unit.

4. The apparatus of claim 1, wherein the first detection unit is triggered up to the multiple times in a cycle of a temperature-modulation.

5. The apparatus of claim 3, further comprising a second beam splitter, wherein the second beam splitter divides the delivered beam from the sample loading unit into the first detection unit and a second detection unit, and a spectroscope is further provided on a front end of the second detection unit.

6. The device of claim 1, further comprising a filter configured to deliver light having a selective wavelength of the light radiated from the light source.

7. A defect analysis method using heat distribution measurement, the method comprising:

radiating visible light onto a sample to determine whether or not there is a defect through heat distribution characteristics;

supplying a power source for generating a driving signal in order to periodically heat the sample;

detecting light reflected from a surface of the sample; and synchronizing a detection unit with the driving signal of a power supply unit, measuring a change of reflectivity of the sample due to a temperature change based on a defined relation using a phase-lock thermal reflection method; converting the measured change to a heat distribution, and analyzing the positions of the defects by detecting hot spots.

8. The method of claim 7, further comprising:

delivering a beam radiated from a light source to the sample loading unit; and delivering a delivered beam from the sample loading unit to the detection unit.

9. The method of claim 7, further comprising:

triggering the detection unit with multiple times for a cycle of a temperature-modulation.

10. The method of claim 7, further comprising:

calculating a change of a thermoreflectance coefficient for each wavelength using a beam delivered from the sample loading unit.

\* \* \* \* \*